United States Patent
Szameitat et al.

(10) Patent No.: US 6,432,295 B1
(45) Date of Patent: Aug. 13, 2002

(54) PROCESS AND DEVICE FOR ELECTROLYTIC POLISHING OF SURGICAL NEEDLES

(75) Inventors: Horst Szameitat, Hamburg; Stephan Gelahr, Norderstedt, both of (DE)

(73) Assignee: Ethicon Limited, Edinburgh (GB)

( * ) Notice: Subject to any disclaimer, the term of this patent is extended or adjusted under 35 U.S.C. 154(b) by 0 days.

(21) Appl. No.: 09/623,844

(22) PCT Filed: Mar. 5, 1999

(86) PCT No.: PCT/EP99/01381
§ 371 (c)(1),
(2), (4) Date: Nov. 22, 2000

(87) PCT Pub. No.: WO99/46431
PCT Pub. Date: Sep. 16, 1999

(30) Foreign Application Priority Data

Mar. 10, 1998 (DE) .......................... 198 11 210

(51) Int. Cl.⁷ .......................... C25D 17/00; C25F 3/00; C25F 7/00
(52) U.S. Cl. .................. 205/664; 204/202; 204/206; 204/224 M; 204/237
(58) Field of Search ................ 205/664; 204/224 M, 204/237, 202, 206, 198

(56) References Cited

U.S. PATENT DOCUMENTS

| | | | |
|---|---|---|---|
| 3,703,452 A | | 11/1972 | Beroff et al. |
| 4,508,611 A | * | 4/1985 | Johnson et al. ............. 204/202 |
| 4,534,843 A | * | 8/1985 | Johnson et al. ............. 204/202 |
| 4,906,345 A | * | 3/1990 | Gramarossa et al. ........ 204/202 |
| 5,477,604 A | | 12/1995 | Smith et al. |
| 5,935,411 A | * | 8/1999 | Brown et al. ................ 205/672 |

* cited by examiner

Primary Examiner—Donald R. Valentine

(57) ABSTRACT

In a process for the electrolytic polishing of surgical needles, a plurality of unfinished needles, which are arranged side by side and are secured to at least one web (6, 7) in their end-regions lying opposite the needle tips, are moved with the help of the web (6, 7) through an acid-containing polishing bath (22) which is electrically connected to an electrode. The web (6, 7) is guided above the polishing bath (22). The unfinished needles dip at least with the needle tips into the polishing bath (22). Above the polishing bath (22) and alongside the web (6, 7), a metal ribbon (40) connected as a counter-electrode provides an electrical connection with the unfinished needles.

20 Claims, 3 Drawing Sheets

PROCESS AND DEVICE FOR ELECTROLYTIC POLISHING OF SURGICAL NEEDLES

Figure 1:
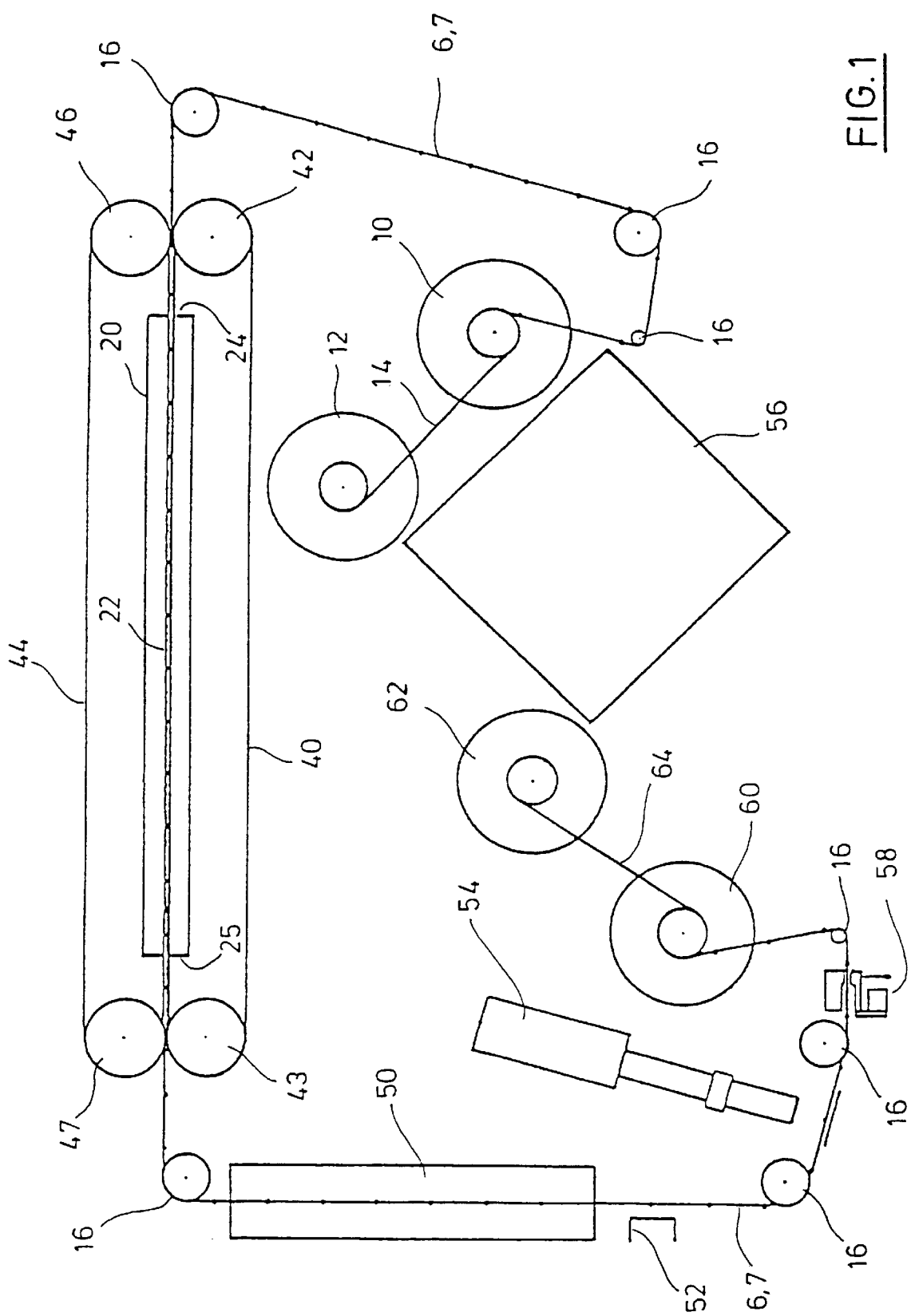

The invention relates to a process for the electrolytic polishing of surgical needles and to a device for carrying out this process.

In the manufacture of surgical needles, unfinished needles are produced first with the help of a needle machine. Each of the unfinished needles already has a needle tip, but can still deviate from the final form in the end-region lying opposite the needle tip. For the further production steps in the manufacture of surgical needles, it has proved advisable to arrange a plurality of unfinished needles side by side and, preferably in their end-regions lying opposite the needle tips, secure them to at least one web. Such a web can for example consist of a double layer of paper and/or plastic, the end-regions of the unfinished needles lying opposite the needle tips being glued in between the two layers of the double layer. If several webs are used, two webs arranged parallel to each other can be used for example. The web with the unfinished needles secured to it can be wound up on a reel. The needles can be well stored in this form and are easily managed in further production steps. In order to release the finished or largely completed surgical needles from the webs towards the end of the manufacturing process, the needles can for example be severed or cut off.

In order to improve the surface properties of the unfinished needles, the unfinished needles must be polished at least in the region of the needle tips (i.e. in the region which is used for the completed surgical needles or is essential). This can take place by treating the unfinished needles secured to at least one web in an acid-containing polishing bath which is electrically connected to an electrode. The unfinished needles serve as counter-electrode. The problem is that as a rule the web has no or only a slight electrical conductivity and therefore every unfinished needle has to be brought individually into electrical contact with a counter-electrode. As the web moves with the unfinished needles, breaks in the electrical connection between an unfinished needle and the counter-electrode can easily result, which reduces the quality of the unfinished needle concerned. As a consequence of this, a substantial number of unfinished needles have to be sorted out after the polishing, which can result in substantial costs.

The object of the invention is to provide a process and a device for the electrolytic polishing of surgical needles in which unfinished needles are used which are secured to a web or several webs in the manner described and as a result of which a reliable electrical contact is produced between the individual unfinished needles and a counter-electrode.

This object is achieved by a process for the electrolytic polishing of surgical needles having the features of claim 1 and by a device having the features of claim 18. Advantageous versions are given in the dependent claims.

With the process according to the invention for the electrolytic polishing of surgical needles, a plurality of unfinished needles which are arranged side by side and, preferably in their end-regions lying opposite the needle tips, are secured to at least one web, are moved with the help of the web through an acid-containing polishing bath which is electrically connected to an electrode. The web is guided above the polishing bath. The unfinished needles dip at least with the needle tips into the polishing bath. Above the polishing bath and alongside the web, a metal ribbon connected as a counter-electrode produces an electrical connection with the unfinished needles.

Because the metal ribbon connected as a counter-electrode is a component independent of the web, a good electrical contact with the unfinished needles can be achieved without major expenditure even if the web is an electrical insulator.

The metal ribbon is preferably a continuous ribbon which is guided by means of rolls alongside the web. It is particularly advantageous if the metal ribbon travels at the same speed as the web. To this end, the metal ribbon can be driven separately from the web or alternatively follow passively, in which case it is taken along by friction forces with the unfinished needles moved by means of the web.

In a preferred version, an elastic ribbon located on the side of the web lying opposite the metal ribbon presses the unfinished needles against the metal ribbon. The elastic ribbon is preferably a continuous ribbon which is guided by means of rolls alongside the web and is preferably pressed towards the metal ribbon by means of individually adjustable pressure rolls and preferably travels at the same speed as the web. A particularly good and certain contact between the metal ribbon and the individual unfinished needles is effected by the elastic ribbon.

The unfinished needles preferably enter the polishing bath through a slit-like opening in one end face of a tank containing the polishing bath and leave the polishing bath via a slit-like opening in the opposite end face of the tank. The liquid flowing out of the openings is collected and pumped back into the tank. This configuration has the advantage that the unfinished needles can be moved into the polishing bath without the web having to be raised and then lowered again in order that the needle tips surmount the edge of the tank. A continuous method of operation is made possible, as a result of which the process can be carried out quickly, reliably and at favorable cost. Preferably, at least one of the slit-like openings is arranged in a height-adjustable plate, so that the level of the liquid in the polishing bath can be set by adjusting the height of the plate.

The polishing bath can contain phosphoric acid, sulphuric acid and/or glycolic acid. It preferably contains a mixture of these constituents. A bare metal surface is created in the polishing bath by means of electrolysis, as a result of which the region of the unfinished needles which dips into the polishing bath is polished.

After leaving the polishing bath, the unfinished needles can be rinsed, preferably by being moved through a water bath. Acid residues are removed from the needle surfaces in this way. The unfinished needles are preferably dried after being rinsed, e.g. by being moved through an air flow.

The process for the electrolytic polishing of surgical needles can be carried out completely automatically, the untreated needles being transportable prior to entry into the polishing bath and afterwards with the help of the web. It is particularly advantageous if, at the beginning, the web with the unfinished needles secured to it is provided wound up on a reel and if, when the process is finished, the web with the unfinished needles secured to it, which are polished at this point, is wound up onto a reel again. For this, the at least one web with the unfinished needles secured to it is unwound from a reel prior to the entry of the unfinished needles into the polishing bath, an inter-mediate layer which is preferably located between the turns of the web on the reel preferably being wound up onto a separate reel. The intermediate layer prevents the unfinished needles from chafing against one another and becoming entangled. Accordingly, the at least one web with the polished unfinished needles secured to it can finally be wound up on a reel, an intermediate layer preferably being fed from a second reel, which intermediate layer is wound onto the reel between the individual turns of the web.

The polished unfinished needles can also be monitored by a video camera, e.g. after they have been dried. Defective unfinished needles can easily be severed in the region projecting beyond the web, so that it is not necessary to detach from the web the end-region of the unfinished needle concerned lying opposite the needle tip.

The invention is described more precisely in the following with the help of an embodiment. The drawings show in FIG. 1 a schematic plan view of a device for carrying out the process according to the invention for the electrolytic polishing of surgical needles, FIG. 2 a schematic longitudinal section through the tank containing the polishing bath and the associated equipment, FIG. 3 an enlarged view of the right-hand region from FIG. 2, in which the unfinished needles guided above the polishing bath are additionally shown, FIG. 4 an enlarged partial view from FIG. 3 and FIG. 5 a schematic front view of the tank containing the polishing bath with associated equipment.

A device for carrying out the process according to the invention for the electrolytic polishing of surgical needles is schematically represented in FIGS. 1 to 5. This device is described in detail in the following, in the order in which the individual components appear when carrying out the process. In this way, the process is illustrated at the same time.

The process for the electrolytic polishing of surgical needles is applied to prefabricated unfinished needles 1. As can best be seen from FIG. 4, each of the unfinished needles 1 has a needle tip 2 which, in the embodiment, lies in a curved region. The unfinished needles 1 are arranged side by side and secured to at least one web in their end-regions 3 lying opposite the needle tips. Two webs are used in the embodiment, namely an upper web 6 and a lower web 7, hereinafter designated web 6, 7. The web 6, 7 (i.e. both the upper web 6 and the lower web 7) consists of a double layer of paper or plastic. The end-regions 3 of the unfinished needles 1 are glued in between the two layers of the double layer, e.g. with the help of an adhesive glue. The unfinished needles 1 are secured to the web 6, 7 in the course of prefabrication, which is not a subject of this process. Storage takes place on a reel on which a web 6, 7 with the unfinished needles 1 secured to it is wound up. In later production steps, which are likewise not a subject of this process, the unfinished needles 1 can be separated from the web 6, 7 in question.

FIG. 1 gives an overview of the process for the electrolytic polishing of surgical needles and of the device used for this. At the beginning of the process, the unfinished needles 1 that are to be polished are located at a web 6, 7, as described previously, which is wound up on a reel 10. In the course of the process, the web 6, 7 is unwound from the reel 10, the unfinished needles 1 at the web 6,7 being transported through the device, so that the individual process steps can be carried out thereon.

Located alongside the reel 10 is a reel 12 onto which an intermediate layer 14 is wound up, while the web 6, 7 is unwound from the reel 10. The intermediate layer 14 is arranged between the individual turns of the web 6, 7 on the reel 10 and prevents the untreated needles 1 from chafing against one another. The intermediate layer 14 can be made e.g. from paper, plastic or metal foil.

Starting from the reel 10, the web 6, 7 is guided through the device by guide rolls 16. The guide rolls 16 can be set to simply hold or deflect the web 6, 7, but it is also possible that individual or all guide rolls 16 are driven in order to move the web 6, 7 through the device. Alternatively, the transport of the web 6, 7 can take place through the reel on which the web 6, 7 is wound up when the process is finished, see below.

After the unfinished needles 1 have left the reel 10, they are transported to a tank 20 with the help of the web 6, 7 and of the guide rolls 16. Located in the tank 20 is a polishing bath 22, see also FIGS. 2 to 5. The polishing bath 22 contains an acid, preferably a mixture of phosphoric acid, sulphuric acid and glycolic acid or a mixture of phosphoric acid and glycolic acid. In the tank 20, the polishing bath 22 is electrically connected to an electrode. This electrode is connected as a cathode at which hydrogen is released during the electrolytic polishing process. The unfinished needles 1, which dip into the polishing bath 22 with their region to be polished (see below), are connected as a counter-electrode, i.e. as an anode, as explained in detail below. The electrolytic polishing process as such is generally known, for which reason it will not be discussed in more detail below.

A slit-like opening is located in each of the end faces 24 and 25 of the tank 20. The slit-like opening 26 in the end face 24 is shown in detail in FIGS. 3 to 5. The slit-like opening 26 is milled out from a plate 27 which is provided with two oblong holes 28. The plate 27 is secured to the end face 24 of the tank 20 by two screws 29 which pass through the oblong holes 28.

This arrangement makes it possible to adjust the height of the plate 27 and thus set the level 30 of the polishing bath 22. The surface or level 30 of the polishing bath 22 actually extends only slightly beyond the lower end of the slit-like opening 26, since liquid 31 flows out of the polishing bath 22 at this point, see in particular FIG. 3 and FIG. 4.

Figure 2:
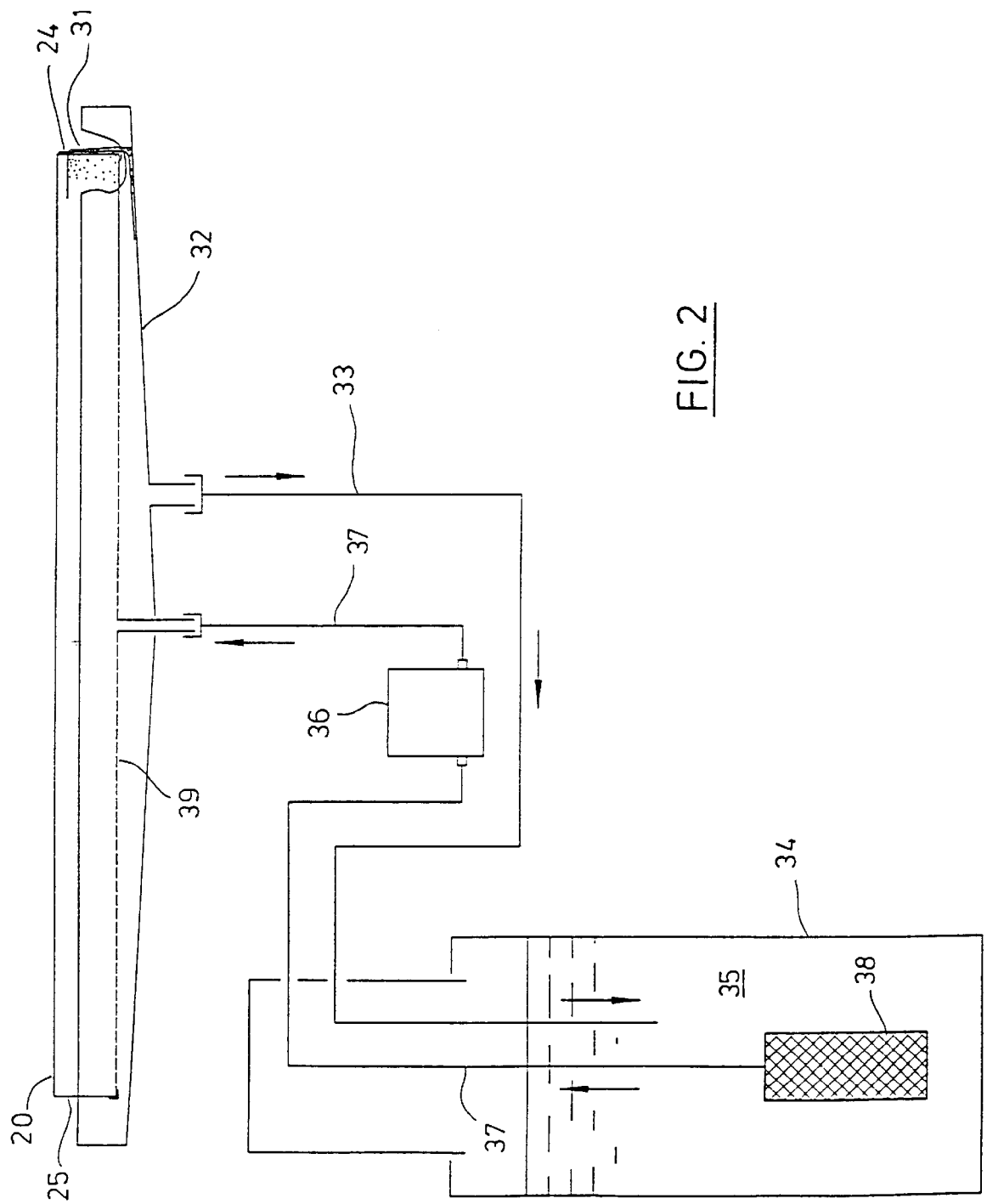
Figure 3:
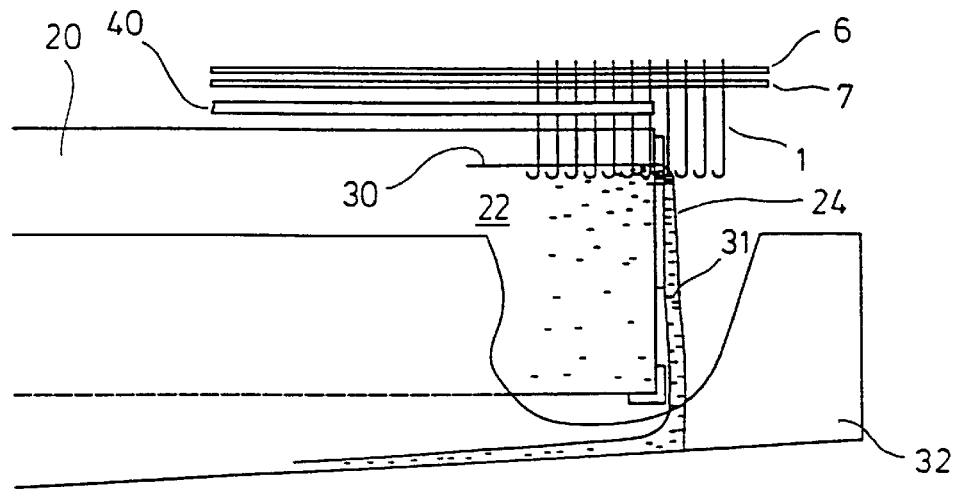

The outflowing liquid 31 is collected in a trap 32, see FIG. 2 and FIG. 3. The region of the trap 32 in the vicinity of the slit-like opening 26 is drawn broken open in FIG. 2 and FIG. 3 in order to illustrate it better. The trap 32 is connected to a discharge line 33 which leads to an acid container 34. Located in the acid container 34 is polishing bath liquid 35 which has the same composition as the polishing bath 22 in the tank 20. With the help of a pump 36, which is fitted into an inflow line 37, the polishing bath liquid 35 is pumped back into the tank 20. Located at the lower end of the inflow line 37 is a filter 38 which prevents impurities in the polishing bath liquid 35, which come from recycled polishing bath 22, from re-entering the tank 20. The upper end of the inflow line 37 opens into the bottom 39 of the tank 20. The polishing bath liquid 35 is heated, which can take place in the tank 20 and/or in the acid container 34. The pump 36 ensures a uniform mixing of the polishing bath 22 and the polishing bath liquid 35.

When an untreated needle 1 to be polished, which is transported by the web 6, 7, has reached the end face 24 of the tank 20, the region of its needle tip 2 enters the tank 20 via the slit-like opening 26, so that it comes into contact with the polishing bath 22. The polishing bath liquid acts on this unfinished needle 1 until it has reached the end face 25 of the tank 20. In this period, the electrolytic polishing process takes place in the region of the needle tip 2. For this, the unfinished needle 1 must be in electrical contact with a counter-electrode (anode).

Figure 4:
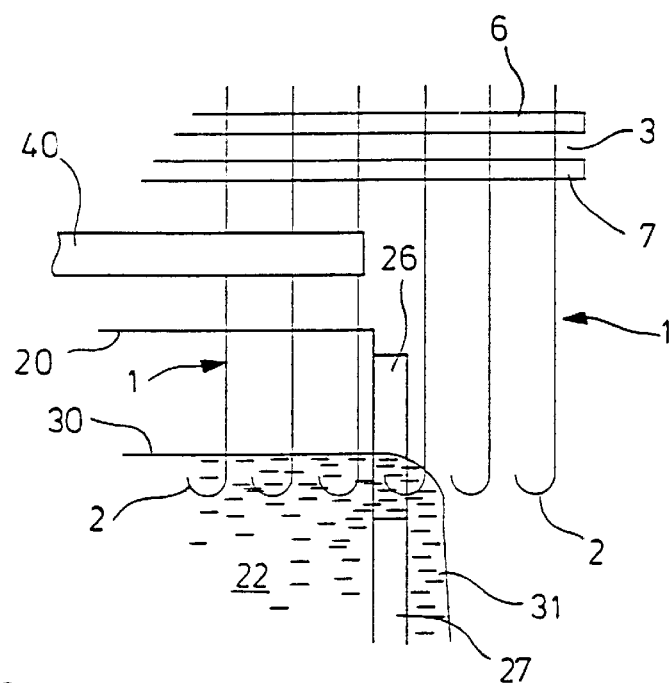

A metal ribbon 40 is connected as counter-electrode, see in particular FIG. 1 and FIG. 4. The metal ribbon 40 is located above the tank 20 with the polishing bath 22 and alongside the web 6, 7. The metal ribbon 40 is designed as a continuous ribbon which is guided round two deflector rolls 42 and 43. Other rolls preferably serve to better guide and stabilize the metal ribbon, but these are not shown in the Figures. The metal ribbon 40 can be actively moved, for example by driving one of the deflector rolls 42 and 43. The metal ribbon 40 preferably travels at the same speed as the web 6, 7. However, if there is adequate friction between the metal ribbon 40 and the unfinished needles 1 which touch it, an active drive is dispensable, since in this case the metal ribbon 40 is taken along by the unfinished needles 1. If the web 6, 7 and the metal ribbon 40 have the same speed, the unfinished needles 1 do not shift or twist relative to the metal ribbon 40, so that a particularly good electrical contact comes about between the unfinished needles 1 and the metal ribbon 40. This also makes possible a problem-free handling of the needles in later process steps, as the unfinished needles 1 are not twisted relative to the web 6, 7. The supply of current to the metal ribbon 40 is not shown in the Figures; it can take place for example via a slip ring which is arranged at the shaft of the deflector roll 42 or 43.

Figure 5:
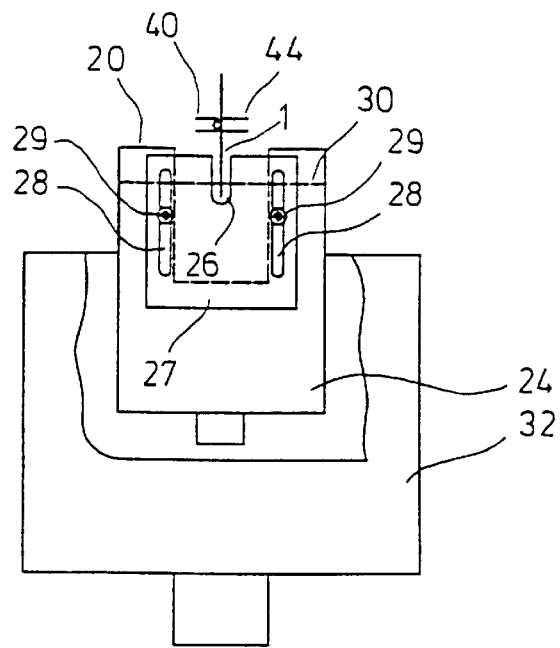

In order that a certain electrical contact between the unfinished needles 1 and the metal ribbon 40 comes about, an elastic ribbon 44 presses the unfinished needles 1 against the metal ribbon 40 on the side of the web 6, 7 lying opposite the metal ribbon 40, see in particular FIG. 1, but also FIG. 5. The elastic ribbon 44 is preferably made from rubber and also designed as a continuous ribbon which is guided by two deflector rolls 46 and 47. Other rolls, which are not shown in the Figures, can be located between the deflector rolls 46 and 47. These rolls are preferably individually adjustable, in order that the bearing pressure with which the elastic ribbon 44 presses the unfinished needles 1 against the metal ribbon 40 can be optimized. The elastic ribbon 44 preferably also moves at the same speed as the web 6, 7, wherein driving can be effected, as in the case of the metal ribbon 40, in an active or passive manner.

In the embodiment, the metal ribbon 40 and the elastic ribbon 44 are arranged underneath the web 6, 7. If the end-regions 3 of the unfinished needles 1 extend to an adequate extent upwards beyond the web 6, 7, it is also possible to locate the metal ribbon 40 and the elastic ribbon 44 in this zone above the web 6, 7.

After the unfinished needles 1 have left the region of the tank 20 via the end face 25, they are transported by the web 6, 7 to a tank 50 which contains warm water. The warm water serves to rinse off unwanted residues of the polishing bath and is constantly supplied fresh to the tank 50. In the embodiment, the warm water is fed into the tank 50 against the direction of travel of the web 6, 7. Similarly to tank 20, the tank 50 is fitted at its end faces with slit-like openings which permit a problem-free entry of the lower regions of the unfinished needles 1 into the tank 50 and a problem-free exit from the tank 50. The water flowing out of these slit-like openings is collected and removed. Located behind the tank 50 is a nozzle apparatus 52, with the help of which hot air is blown onto the polished and rinsed unfinished needles 1 in order to dry the unfinished needles 1.

The unfinished needles 1 can be inspected and examined with the help of a video camera 54. The video camera 54 is connected to a monitor 56. Should a specific unfinished needle 1 not have the necessary quality, perhaps because it was only inadequately polished or because the needle geometry is different, it can be cut off by means of a cutting apparatus 58 while it is moved through the cutting apparatus 58 by the web 6, 7. The end-region 3 of this unfinished needle 1 remains on the web 6, 7.

Finally, the web 6, 7 with the polished unfinished needles 1 located on it is wound up on a reel 60. In order to prevent the unfinished needles 1 of neighbouring turns scraping against one another and becoming entangled, an intermediate layer 64 (e.g. made of paper, plastic or metal foil), which comes to rest between the individual turns of the web 6, 7 with the polished unfinished needles 1 on the reel 60, is fed from a reel 62.

This description shows how the process according to the invention for the electrolytic polishing of surgical needles can proceed on a device for carrying out this process. In the embodiment, at the beginning the web 6, 7 with the not yet polished unfinished needles 1 secured to it was wound up on the reel 10. Upon completion, the unfinished needles 1 are polished in the regions of their needle tips 2 and are, still secured to the web 6, 7, wound up on the reel 60. They can be stored on the reel 60 and subjected to subsequent process steps.

What is claimed is:

1. Process for the electrolytic polishing of surgical needles, in which a plurality of unfinished needles (1) which are arranged side by side and, preferably in their end-regions (3) lying opposite the needle tips (2), are secured to at least one web (6, 7) are moved with the help of the web (6, 7) through an acid-containing polishing bath (22) which is electrically connected to an electrode, the web (6, 7) being guided above the polishing bath (22) and the unfinished needles (1) dipping at least with the needle tips (2) into the polishing bath (22), and in which, above the polishing bath (22) and alongside the web (6, 7), a continuous metal ribbon (40) guided by means of rolls (42), 43) alongside the web (6, 7) and connected as counter-electrode providing an electrical connection with the unfinished needles (1).

2. Process according to claim 1, characterized in that the metal ribbon (40) travels at the same speed as the web (6, 7).

3. Process according to claim 1, characterized in that an elastic ribbon (44) located on the side of the web (6, 7) lying opposite the metal ribbon (40) presses the unfinished needles (1) against the metal ribbon (40).

4. Process according to claim 3, characterized in that the elastic ribbon (44) is a continuous ribbon which is guided by means of rolls (46, 47) alongside the web (6, 7) and which is preferably pressed towards the metal ribbon (40), by means of individually adjustable pressure rolls.

5. Process according to claim 4, characterized in that the elastic ribbon (44) travels at the same speed as the web (6, 7).

6. Process according claim 1, characterized in that the unfinished needles (1) enter the polishing bath (22) through a slit-like opening (26) in one end face (24) of a tank (20) containing the polishing bath (22) and leave the polishing bath (22) via a slit-like opening in the opposite end face (25) of the tank (20), the liquid (31) flowing out of the openings (26) being collected and pumped back into the tank (20).

7. Process according to claim 6, characterized in that at least one of the slit-like openings (26) is arranged in a height-adjustable plate (27) and the level (30) of the polishing bath (22) is set by adjusting the height of the plate (27).

8. Process according to claim 1, characterized in that the polishing bath (22) contains at least one of the following constituents: phosphoric acid, sulphuric acid, glycolic acid.

9. Process according to claim 1, characterized in that, after leaving the polishing bath (22), the unfinished needles (1) are rinsed, preferably by being moved through a water bath (50).

10. Process according to claim 9, characterized in that the unfinished needles are dried after being rinsed, preferably by being moved through an air flow (52).

11. Process according to claim 1, characterized in that a double layer made of paper and/or plastic is used as a web (6, 7), the end-regions (3) of the unfinished needles (1) lying opposite the needle tips (2) being glued in between the two layers of the double layer.

12. Process according to claim 1, characterized in that two webs (6, 7) arranged parallel to each other are used.

13. Process according to claim 1, characterized in that the at least one web (6, 7) with the unfinished needles (1) secured to it is unwound from a reel (10) prior to the entry of the unfinished needles (1) into the polishing bath (22), an intermediate layer (14) preferably located between the turns of the web (6, 7) on the reel (10) being preferably wound up onto a separate reel (12).

14. Process according to claim 1, characterized in that the polished unfinished needles (1) are monitored with the help of a video camera (54).

15. Process according to claim 1, characterized in that defective unfinished needles (1) are severed in the region projecting beyond the web (6, 7) underneath the web (6, 7).

16. Process according to claim 1, characterized in that the at least one web (6, 7) with the polished unfinished needles (1) secured to it is finally wound up on a reel (60), an intermediate layer (64) preferably being fed from a second reel (62), which intermediate layer is wound onto the reel (60) between the individual turns of the web (6, 7).

17. Device comprising:
- a tank (20) for an acid-containing polishing bath (22) which can be brought into electrical connection with an electrode,
- a guiding and movement apparatus (16) for at least one web (6, 7), at which a plurality of unfinished needles (1) are arranged side by side and to which they are secured, preferably with their end-regions (3) lying opposite the needle tips (2), the guiding and movement apparatus (16) being adapted to guide the web (6, 7) above the polishing bath (22) and to move the web (6, 7) so that the unfinished needles (1) are moved through the polishing bath (22) with/the help of the web (6, 7) and dip into the polishing bath (22) at least with the needle tips (2), and
- a continuous metal ribbon (40) guided by means or rolls (42, 43) alongside the web (6, 7), arranged above the tank (20) and alongside the web (6; 7), which can be connected as a counter-electrode and brought into electrical connection with the unfinished needles (1).

18. Device according to claim 18, characterized by an elastic ribbon (44), located on the side of the web (6, 7) lying opposite the metal ribbon (40), which is adapted to press the unfinished needles (1) against the metal ribbon (40).

19. Device according to claim 18, characterized in that the elastic ribbon (44) is a continuous ribbon, guided by means of rolls (46, 47) alongside the web (6, 7), which is preferably pre-tensioned towards the metal ribbon (40) by means of individually adjustable pressure rolls.

20. Device according to one of claims 17 to 19, characterized in that the tank (20) has slit-shaped openings (26) at both end faces (24, 25) and in that the device has an apparatus for collecting (32) the liquid (31) flowing out of the openings (26) and for pumping (36) the liquid back into the tank (20), preferably at least one of the slit-shaped openings (26) being arranged in a height-adjustable plate (27).

* * * * *